Figure 1:
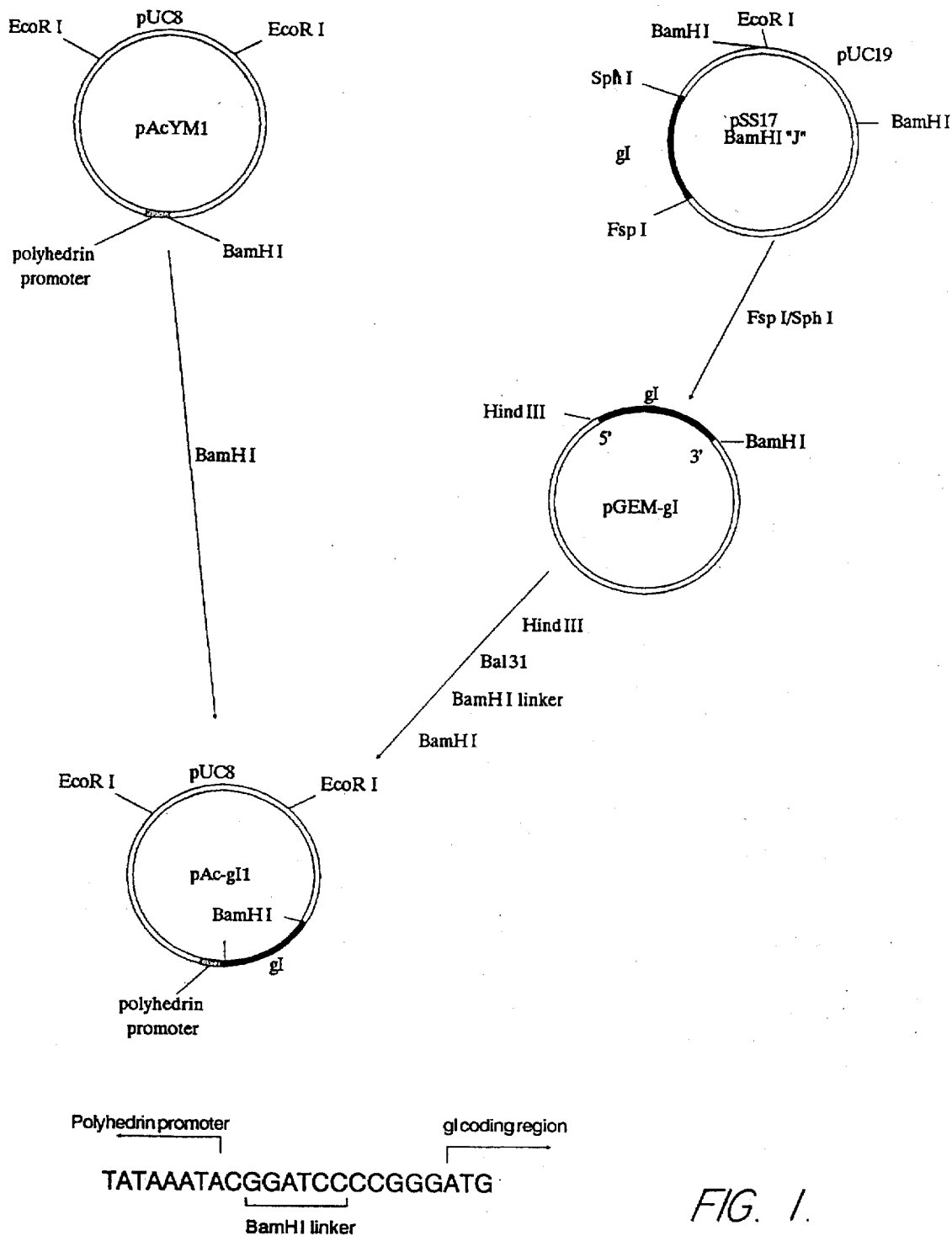
Figure 2:
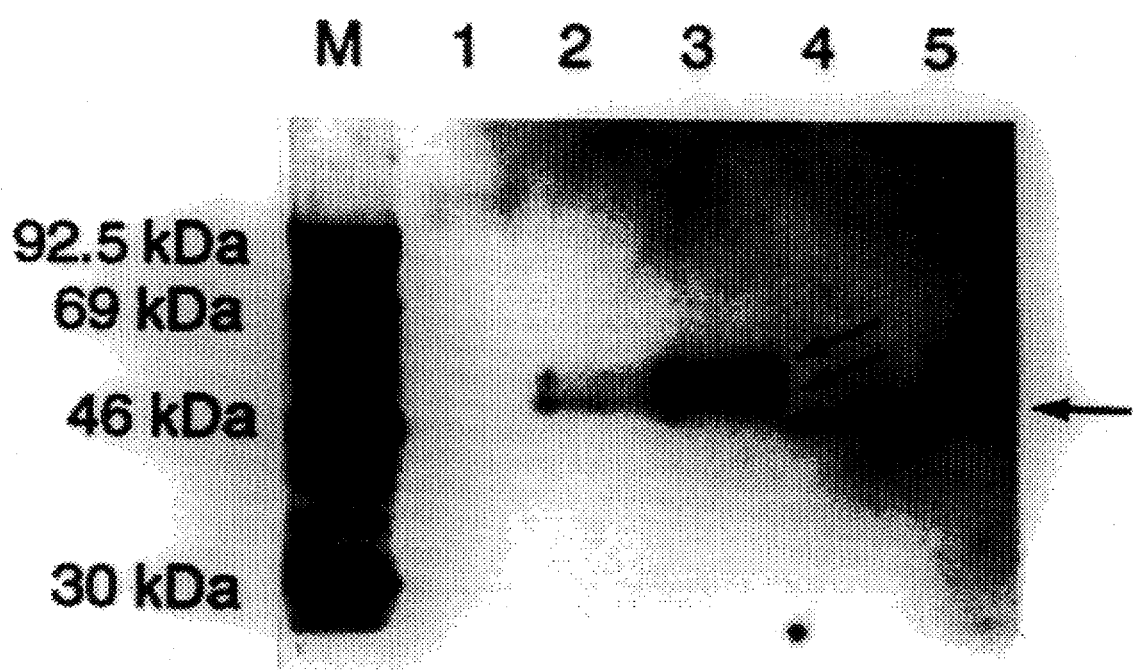

United States Patent [19]

Nesburn et al.

[11] Patent Number: 5,672,349

[45] Date of Patent: Sep. 30, 1997

[54] PROCESS FOR THE EXPRESSION OF HERPES SIMPLEX VIRUS TYPE 1 GLYCOPROTEIN I AND METHODS OF USE

[75] Inventors: Anthony Bart Nesburn, Malibu; Steven Lewis Wechsler, Westlake Village; Homayon Ghiasi, Los Angeles, all of Calif.

[73] Assignee: Cedars Sinai Medical Center, Los Angeles, Calif.

[21] Appl. No.: 310,370

[22] Filed: Sep. 22, 1994

Related U.S. Application Data

[63] Continuation of Ser. No. 852,999, Mar. 18, 1992, abandoned, which is a continuation-in-part of Ser. No. 829,947, Feb. 3, 1992.

[51] Int. Cl.$^6$ .................... A61K 39/245; C12N 15/38; C12P 21/02
[52] U.S. Cl. .................... 424/186.1; 424/231.1; 435/69.1; 435/172.3; 435/69.3; 514/12
[58] Field of Search .................... 435/235, 172.3, 435/240.2, 65.1, 69.1, 69.3; 530/395; 514/2, 12; 424/186.1, 231.1

[56] References Cited

U.S. PATENT DOCUMENTS

| | | | |
|---|---|---|---|
| 4,859,587 | 8/1989 | Roizman | 435/69.3 |
| 4,891,315 | 1/1990 | Watson et al. | 435/69.3 |

FOREIGN PATENT DOCUMENTS

| | | |
|---|---|---|
| 0 243 155 | 10/1987 | European Pat. Off. . |
| 0 297 924 | 1/1989 | European Pat. Off. . |
| WO85/04587 | 10/1985 | WIPO . |

OTHER PUBLICATIONS

Atherton, "Protection from retinal necrosis by passive transfer of monoclonal antibody specific for herpes simplex virus glycoprotein D," Current Eye Research 11(1):45–52 (1992).
Foster et al., "Immunomodulation of experimental murine herpes simplex keratitis: H. Glycoprotein D protection," Current Eye Research 2(11):1051–1061 (1988).
Ghiasi et al., "Expression of herpes simplex virus type 1 glycoprotein B in insect cells," Virus Research 22(1):35–39 (1991).
Ghiasi et al., "High Level Expression of Each of the Seven Herpes Simplex Virus Glycoproteins in Insect Cells Using Baculovirus Expression Vectors: Subsequent Use as Vaccines," Invest. Ophthalmol. Visual Sci., 32(4):806 (1991).
Ghiasi et al., "Immunoselection of recombinant baculoviruses expressing high levels of biologically active herpes simplex virus type 1 glycoprotein D," Arch. Virol. 121:163–178 (1991).
Kino et al., "Immunogenicity of herpes simplex virus glycoprotein gB-1-related protein produced in yeast," Vaccine 2(2): 155–160 (1989).
Lausch et al., "Prevention of Herpes Keratitis by Monoclonal Antibodies Specific for Discontinuous and Continuous Epitopes on Glycoprotein D," Invest. Ophthal. Visual Sci. 32(10):2735–2740 (1991).

Nesburn et al., "Efficacy and Safety of 'Therapeutic' Systemic HSV Vaccines in the Rabbit Ocular Recurrence Model," Invest. Ophthalmol. Visual Sci. 32(4):854 (1991).
Krishna et al. (1989) J. gen. Virol. 70: 1805–1814.
Ghiasi et al. (1992) Baculovirus–expressed glycoprotein H of herpes simplex virus type 1 (HSV–1) induces neutralizing antibody and delayed type hypersensitivityresponses, but does not protect immunized mice against lethal HSV–1 challenge. Journal of Ge.
Krishna et al (1989) J. gen Virol. 70 1805–1814.
Klein, R.J., Reinfections and site-specific immunity in herpes simplex virus infections. Vaccine, 7:380–381 (1989).
Stanberry, L.R. et al., Herpes simplex virus glycoprotein treatment of recurrent genital herpes. J. Infec. Dis., 157:156–63 (1988).
Kern, A.B. et al., Vaccine Therapy in Recurrent Herpes Simplex. Arch. Derm., 89:844–845 (1964).
Frenkel, L. et al., A randomized double blind, placebo–controlled phase 1 trial of a herpes simplex virus purified glycoprotein (gD1) vaccine. Interscience Conf. on Antimicrobial Agents & Chemo., 206 (1990).
Berman, P.W. et al., Efficacy of Recombinant Glycoprotein D Subunit Vaccines on the Development of Primary, Recurrent, and Latent Genital Infections With Herpes Simplex Virus Type 2 in Guinea Pigs. J. Infec. Dis., 157(5):897–902 (May 1988).
Blacklaws, B. et al., Immunogenicity of herpes simplex type 1 glyco–proteins expressed in vaccinia virus recombinants. Virology, 177:727–736 (1990).
Stanberry, L.R. et al., Heterologous Versus Homologous Herpes Simplex Virus Glycoprotein Immunotherapy of Recurrent Genital Herpes. Pediatr. Res., 25:191A, Part 2 (1989).
Rock, D.L., Nesburn, A.B. et al., Detection of latency related viral RNAs in trigeminal ganglia of rabbits latently infected with herpes simplex virus type 1. J. Virol., 61:3820–26 (1987)..
Matsuura, Y. et al., Baculovirus expression vectors: the requirements for high level expression of proteins, including glycoproteins. J. Gen. Virol., 68:1233–50 (1987).
Lee, G.T. et al., Location of the structural genes for glycoproteins gD and gE and for other polypeptides in the S component of herpes simplex virus type 1 DNA. J. Virol., 43:41–49 (1982).
Mathews, J.T. et al., Synthesis and processing glycoprotein D of herpes simplex virus types 1 and 2 in an in vitro system. J. Virol., 48:521–53 (1983).

(List continued on next page.)

Primary Examiner—Robert A. Wax
Assistant Examiner—G. E. Bugaisky
Attorney, Agent, or Firm—Lyon & Lyon

[57] ABSTRACT

A process for obtaining Herpes Simplex virus type 1 (HSV–1) glycoprotein I (gI) from cells which have been infected or transformed with a recombinant Baculovirus is disclosed. The gI produced is then isolated and purified for use in immunotherapy against HSV infections.

21 Claims, 3 Drawing Sheets

OTHER PUBLICATIONS

Ghiasi, H., et al., Cell surface expression of herpes simplex virus type 1 glycoprotein H in recombinant baculovirus infected cells. *Virology*, 185:187–194 (1991).

Morein, B. et al., Iscom, a novel structure for antigenic presentation of membrane proteins from enveloped viruses. *Nature*, 308:457–60 (1984)..

Shimormura, Y. et al., Shedding by iontophoresis of 6-hydroxdopamine followed by topical epinephrine. *Invest. Ophthalmol.*, 24:1588–90 (1983).

Nesburn, A.B. et al., Isolation of herpes simplex virus: Isolation free rabbit trigeninal ganglia between episodes of recurrent ocular infection. *Arch. Ophthalmol.*, 88:412–17 (1972).

Nesburn, A.B. et al., Ocular safety and efficacy of an HSV–1 gD vaccine during primary and latent infection. *Invest. Ophthalmol. Vis. Sci.*, 31:77–82 (1990).

Sullivan, V. and Smith, G.L. The Herpes Simplex Virus Type 1 US7 Product is a 66K Glycoprotein and Is A Target for Complement–dependent Virus Neutralization. *J. Gen. Virol.*, 69:859–867 (1988).

Johnson, D.C. and Feenstra, V. Identification of a Novel Herpes Simplex Virus Type 1 induced glycoprotein which complexes with gE and binds immunoglobulin. *J. Virol.*, 61:2208–2216 (1987).

5,672,349

PROCESS FOR THE EXPRESSION OF HERPES SIMPLEX VIRUS TYPE 1 GLYCOPROTEIN I AND METHODS OF USE

This application is a continuation of application U.S. Ser. No. 07/852,999 filed Mar. 18, 1992, now abandoned which is a continuation-in-part of application Ser. No. 07/829,947, filed Feb. 3, 1992. All of the above applications are expressly incorporated herein by reference.

FIELD OF THE INVENTION

The present invention is in the fields of infectious diseases and molecular biology.

BACKGROUND OF THE INVENTION

A. Herpes Simplex Virus Type 1 (HSV-I) Glycoprotein I

Glycoprotein I (gI) is one of ten documented herpes simplex virus type 1 (HSV-1) glycoproteins. In HSV-1 infected cells, gI is present as an unglycosylated peptide having a molecular weight of 41 kDa. The unglycosylated polypeptide is partially glycosylated to produce a precursor gI of approximately 55 kDa, which is then further glycosylated to the mature gI with an apparent molecular weight of 65 kDa.

The ten HSV glycoproteins are located on the surface of the virus, some of which are reported to be the primary inducers and targets of both humoral (antibody) and cell-mediated immune responses to HSV-1 infection. The HSV-1 glycoproteins E and I form a complex that can bind the Fc portion of immunoglobulin G. While gE alone can act as an Fc receptor, gI appears to enhance this activity; yet, no Fc receptor activities have been detected with gI alone. Moreover, Blacklaws et al. found that vaccinia expressed gI produced no protective response in immunized mice. BLACKLAWS, B. A., KRISHNA, S., MINSON, A. C. and NASH, A. A. Immunogenicity of Herpes simplex virus type 1 glycoproteins expressed in vaccinia virus recombinants. Virology, 177: 727–736 (1990).

Glycoprotein I has been expressed by only one other group, Sullivan and Smith, in a vaccinia expression system, and reported that the gI neutralization antibody was completely complement dependent. SULLIVAN, V. and SMITH, G. L. The Herpes Simplex Virus Type 1 US7 Gene Product is a 66K Glycoprotein and Is a Target for Complement-dependent Virus Neutralization. J. Gen. Virol., 69:859–867 (1988). However, their reported neutralization titers were exceptionally low and were determined using unconventional assays. Furthermore, Blacklaws et al., using the same vaccinia recombinant gI constructed by Sullivan and Smith, and using standard assays, obtained neutralization titers of less than 1:2 in the presence of complement.

In contrast to these reports, we have expressed in a baculovirus system, high quantities of gI which is capable of eliciting a strong protective immune response against HSV-1 infection. Mice vaccinated with our recombinant gI induced a strong neutralizing antibody response. The gI neutralization titer was 1:167 in the presence of complement and 1:91 in the absence of complement, appearing therefore to be partially complement dependent. We also found that mice vaccinated with baculovirus recombinant gI showed complete protection against lethal HSV-1 infection. To our knowledge, this is the first report to demonstrate that gI can induce protective immunity in animals against HSV-1 challenge. This ability to produce large quantities of high quality bioactive gI is critical in the development of an effective vaccine against HSV.

B. DNA Technology

Recombinant DNA and associated technologies can be applied to effectively provide the large quantities of high quality bioactive HSV glycoprotein I required for a therapeutic or prophylactic HSV vaccine.

DNA technology involves in part, producing a replicable expression vehicle or transplacement vector by the DNA recombination of an origin of replication, one or more phenotypic selection characteristics, an expression promoter, a heterologous gene insert and remainder vector. The resulting expression vehicle is introduced into cells by transformation allowing a transplacement of the genetic construct from the recombinant baculovirus transplacement vector to the receptor baculovirus. Large quantities of the recombinant vehicle are then obtained by growing the transformant. Where the gene is properly inserted or functionally linked with reference to regulatory elements which govern the transcription and translation of the encoded DNA message, the expression vehicle may produce the polypeptide sequence for which the inserted gene codes. This process of producing the polypeptide is called "expression." The resulting product may be obtained by lysing the host cell, and recovering the product by appropriate purification.

A wide range of host cells can be used, including prokaryotic and eukaryotic organisms. In addition to microorganisms, cultures of cells derived from multicellular organisms, whether vertebrate or invertebrate, may also be used as hosts. Our system involved use of baculovirus, the polyhedrin promotor system and insect cells as host cells to produce high quantities of bioactive gI. To our knowledge, we are the first to demonstrate high levels of protection against lethal HSV-1 challenge using a gI vaccine.

The references cited herein are all incorporated by reference.

SUMMARY OF THE INVENTION

The present invention relates to the production of HSV-1 gI, by recombinant DNA techniques, and its use as an immunogen in a vaccine to protect against HSV-1 and/or HSV-2 infections. Vaccines made from genetically engineered immunogens should be safer than conventional vaccines made from attenuated virus because there is no risk of infection to the recipient; and specifically with the herpes virus, there should be no risk of cervical cancer. Alternatively, the genetically engineered glycoprotein or protein product may be used to produce antibodies for use in passive immunotherapy. The invention also relates to the transformed cell line, which contains the subject transplacement vector, and its cultures which produce HSV-1 gI.

To this end, we constructed a recombinant baculovirus expressing high levels of HSV-1 gI in Sf9 cells. We unexpectedly discovered, however, that vaccination of mice with our expressed gI, demonstrated high levels of protection against lethal HSV-1 challenge. Methods and compositions are therefore provided for the cloning and expression of HSV gI gene in single-cell host organisms. Also described are methods for culturing these novel single-cell organisms to produce the HSV gI gene product as well as methods for the purification of the gene product.

A human host is then preferably inoculated with a vaccine comprising an immunity inducing dose of gI alone or with one or more HSV glycoproteins or proteins by the systemic route, the enteric route or by the ocular route. The vaccine may also comprise one or more adjuvants administered with, before or after the glycoprotein component of the vaccine.

The vaccine of the invention may be conveniently utilized in liquid form, freeze-dried, spray dried or lyophilized form, in combination with one or more suitable preservatives and protective agents to protect the glycoproteins or proteins during processing.

A. Antigen

The baculovirus expressed gI migrated on gels with molecular weights of 52 and 56 kDa. The recombinant gI appeared to be glycosylated, as demonstrated by its susceptibility to both tunicamycin and endoglycosidase H. Indirect immunofluorescence also demonstrated that it was transported to the membrane of Sf9 cells. Mice vaccinated with our expressed gI developed high serum titers of complement-dependent and non-complement-dependent HSV-1 neutralizing antibodies, which protected the mice from lethal HSV-1 challenge.

B. Adjuvants

Vaccines are often administered in an emulsion with various adjuvants. The adjuvants aid in attaining a more durable and higher level of Immunity using smaller amounts of antigen in fewer doses than if the immunogen were administered alone. The adjuvants for use in the present invention include but are not limited to alum, Freund's, MTP-PE and ISCOMs (Quil A). In addition, the vaccine may comprise a liposome or other membrane bound vesicle comprising one or more HSV-1 glycoproteins administered with or without one or more adjuvants to induce the cell mediated immune response.

C. Immunization Routes

The vaccine can be administered by the systemic route, the ocular route either alone or in combination with systemic vaccination, or the enteric route. The systemic route includes but is not limited to subcutaneous, intramuscular or intravenous injection in one or multiple doses. The ocular route includes but is not limited to subconjunctival injection, surface drops, a slow-release device such as a collagen shield, a hydrogel contact lens or an ALZA "Ocusert" in one or multiple doses.

Doses to be administered are variable and depend on the desired effect and on the chosen administration route, with 1 to 3 doses generally comprising the vaccination. However, inoculation doses to humans by injection vary from about 1 µg to 1000 µg. For ocular vaccination, the human dosages vary from about 1 µg to 500 µg; whereas for enteric vaccination, the human dosages vary from about 1 µg to 2000 µg.

It is therefore a general object of the present invention to express high levels of HSV-1 gI.

It is an object of the present invention to express high levels of HSV-1 gI from one virus strain in a single vector system.

It is also an object of the present invention to express high levels of bioactive HSV-1 gI from cells which have been infected or transformed with a recombinant baculovirus.

It is another object of the present invention to obtain a transformed cell line which produces HSV-1 gI.

It is a further object of the present invention to develop an effective vaccine for the treatment or prevention of HSV in a host.

These and other objects will become readily apparent to those skilled in the art from the following description and appended claims.

D. BRIEF DESCRIPTION OF THE DRAWINGS

The present invention will be described with the help of the accompanying drawings in which:

FIG. 1 is a schematic diagram of the construction of the pAc-gI1 recombinant baculovirus transfer vector containing the HSV-1 gI gene. The strategy for the construction of the baculovirus transfer vector (pAc-gI1) containing the complete coding region of HSV-1 gI (■) under control of the baculovirus polyhedrin gene promoter (■) is outlined herein and described in the text. At the bottom of the figure is the sequence of the region near the 5' end of the cloned gI in the baculovirus transfer vector. The 3' end of the baculovirus polyhedron gene promoter, a BamHI linker, and the coding sequence of gI (preceded by five noncoding nucleotides of the gI gene) are indicated.

FIG. 2 is a Western blot analysis of expressed gI in infected insect cells. Insect cells were infected at a multiplicity of infection of 10 with the baculovirus gI recombinant (vAc-gI1), and some monolayers were treated with tunicamycin (0 to 48 h postinfection) or cell extracts were treated with endoglycosidase H as recommended by the manufacturer (Boehringer Mannheim Biochemicals). Briefly, $10^5$ cells were lysed in gel sample buffer, sodium acetate buffer (pH 5.0). Endoglycosidase H was then added and the samples were incubated overnight. Lanes: M, molecular size markers; 1, wild-type-baculovirus-infected insect cells; 2, baculovirus-gI-infected cells 48 h postinfection; 3, baculovirus-infected insert cell; 72 h postinfection; 4, tunicamycin-treated, baculovirus-gI-infected cells (48 h); 5, endoglycosidase H-treated, baculovirus-gI-infected cells 72 h postinfection.

FIGS. 3A, 3B and 3C show immunofluorescence of recombinant baculovirus-infected cells. Acetone-fixed or unfixed infected Sf9 cells were incubated with anti-gI monoclonal antibody followed by fluorescein-conjugated goat anti-mouse immunoglobulin G antibody and examined by fluorescence microscopy as described previously and known in the art. FIG. 3A Recombinant baculovirus-gI-infected cells, total (intracellular) fluorescence; FIG. 3B baculovirus-gI-infected cells, surface fluorescence; FIG. 3C wild-type-baculovirus-infected cells, total fluorescence.

DETAILED DESCRIPTION

The present invention utilizes recombinant DNA techniques to insert a DNA sequence coding for HSV-1 gI or a portion thereof, into a DNA transplacement vector, such that the vector is capable of replicating and directing expression of the gI gene in a foreign host. The resulting recombinant DNA molecule is introduced into insect cells to enable high production of gI, or a portion or molecular variant thereof by the host cells. The gI produced is then isolated and purified for use in immunotherapy against both HSV type 1 and/or type 2.

The Examples set forth below describe use of baculovirus, the polyhedron promoter system and insect cells as host cells. However, it would be well within the skill of the art to use analogous techniques to construct expression vectors for expression of desired gI and gI products in alternative host cell cultures. The following detailed description is, therefore, not to be taken in a limiting sense, and the scope of the present invention is best defined by the appended claims.

A. Viruses and Cells

The E2 strain of *Autographa californica* nuclear polyhedrosis virus (AcNPV) and *Spodoptera frugiperda* clone 9 (Sf9) cells were grown according to procedures known in the art. Plaque purified HSV-1 (strains McKrae and KOS) and Vero cells were grown using standard techniques.

B. Construction of the AcNPV Recombinant Transfer Vector

Plasmid pSS17 was double digested with Fsp I/Sph I and a 1.3 Kb fragment containing the complete coding region of gI was isolated. The resulting fragment was ligated into the Sma I site of pGem-3. Plasmid pGem-gI was linearized with Hind III, digested briefly with Bal 31 exonuclease, and ligated into the unique BamHI site of the vector pAcYM1. Partial sequence analysis indicated that the cloned gI has a short noncoding region of 5 nucleotides at the 5' end and 48 HSV-1 noncoding nucleotides after the gI termination codon at the 3' end.

C. Transfection and Selection of Recombinant Viruses

Sf9 cells were cotransfected with purified infectious baculovirus (AcNPV) DNA and pAc-gI1 plasmid DNA according to procedures known in the art. Following three cycles of polyhedrin-negative plaque purification, two recombinant viruses were obtained. Both recombinants expressed gI with similar properties as determined by Western blotting using anti-gI monoclonal antibody. One of the recombinant baculoviruses was chosen for further study and designated vAc-gI1.

D. Preparation of Viral DNA

Sf9 cells were infected with recombinant virus at an MOI of 10 PFU/cell and incubated at 28° C. for 72 hr. The infected cells were freeze-thawed and centrifuged for 10 min. at 1000×g to remove cell debris. The subsequent procedures used for virus isolation, DNA extraction and blotting are known in the art, and therefore will not be repeated here.

E. Western Blots

Western immunoblot analyses were carried out under denaturing conditions. Samples for SDS-PAGE were disrupted in electrophoresis sample buffer containing 2% SDS and 10% 2-mercaptoethanol and heated at 100° C. for 3 min. Proteins were separated by SDS-PAGE and transferred to nitrocellulose paper by electrophoresis. The nitrocellulose blots were blocked in BLOTTO (5% nonfat dry milk in PBS) and reacted with Fd69 anti-gI monoclonal antibody (a gift from Dr. S. Chatterjee) for 1 hr at 4° C. Bound antibody was detected by reacting the blots with $^{125}$I-protein A for 1 hr at 25° C., followed by autoradiography.

F. Endoglycosidase H (Endo-H) Treatment

Endo-H treatment was done on lysates from Sf9 infected cells (10 PFU/cell; 72 hr post infection) as described by the manufacturer (Boehringer Mannheim Biochemicals). Briefly, 105 cells were lysed in gel sample buffer, Na-acetate (pH 5.0) buffer. Endo-H was then added and the samples were incubated overnight.

G. Tunicamycin Treatment

Infected cells (10 PFU/cell) were incubated in 4 µg/ml tunicamycin in TNM-FH media from 0–48 hr post infection and harvested for SDS-PAGE.

H. Immunofluorescence

Sf9 cells were infected with wild-type AcNPV or recombinant baculoviruses expressing gI (multiplicity of infection of 10 PFU/cell) and incubated for 72 hr. To look at total fluorescence, cells were washed with PBS, fixed with acetone, and incubated with gI monoclonal antibody for 1 hr at 37° C. To examine cell surface immunofluorescence, unfixed, unpermeabilized cells were incubated with anti-gI monoclonal antibody for 1 hr at 4° C., and then fixed with acetone. Slides for total and surface fluorescence were then stained with fluorescein-conjugated goat anti-mouse IgG for 1 hr at 37° C., and examined for fluorescence.

I. Vaccination

Sf9 cells infected for 72 hr with 10 PFU/cell of wild type (AcNPV) or vAc-gI1 were collected, washed and suspended in PBS. Mice (Balb/C, 6–8 weeks old) were vaccinated three times subcutaneously and intraperitoneally (concomitantly) with freeze-thawed whole insect cells expressing gI. Subcutaneous injections were done with 1×10$^6$ cells mixed with Freund's complete adjuvant on day 0 or mixed with Freund's incomplete adjuvant on days 21 and 42. Intraperitoneal injections were done using 1×10$^6$ cells in PBS on the same day. Mock vaccinated mice were similarly inoculated with Sf9 cells infected with wild type baculovirus. A positive control group was immunized three times intraperitoneally with 2×10$^5$ PFU of KOS. Sera were collected three weeks after final vaccination and pooled for each group.

J. Serum Neutralization Assay

For in vitro serum neutralization assays, heat inactivated pooled sera were diluted in MEM, and mixed with 500 PFU of HSV-1 strain KOS, for 30 min at 37° C., Two and one half percent of heat-inactivated or fresh guinea pig complement was added and the mixture incubated for another 30 min. Duplicate samples were added to CV-1 cells in 24-well microtiter plates and residual HSV-1 infectivity was assayed. The plates were incubated at 37° C. for 72 hr, strained with 1% crystal violet, and plaques were counted.

K. HSV-I Challenge

Three weeks after the final vaccination, mice were challenged intraperitoneally with 2×10$^6$ PFU of HSV-1 (McKrae strain). Challenged mice were monitored for a period of two weeks.

Results

A. Construction of Recombinant Viruses Expressing gI

The strategy for the construction of the baculovirus transfer vector containing the complete gI open reading frame is shown in FIG. 1. A complete DNA copy of the gI gene was isolated by restriction enzyme digestion with Fsp I/Sph I. The resulting fragment containing the complete coding region of HSV-1 gI (black) was blunt-ended into the Sma I site of pGem-3. Plasmid pGem-gI was linearized with Hind III, digested briefly with Bal 31 exonuclease, and BamHI linker was added. The resulting DNA was then inserted into the BamHI site of the pAcYM1 vector. (See FIG. 1 and the Detailed Description above). Restriction enzyme analysis and partial sequencing confirmed that this construct contains the entire sequence of the gI gene. It has a noncoding region of 5 nucleotides in front of the first ATG. This is followed by the complete coding region of 1170 nucleotides. To transfer the gI gene into the baculovirus AcNPV genome, Sf9 cells were cotransfected with pAc-gI1DNA and infectious AcNPV DNA. Two putative recombinant viruses were selected by three cycles of polyhedron-negative plaque purification. Both recombinant baculoviruses expressed gI with similar properties as determined by Western blotting. One was arbitrarily chosen for subsequent study and designated vAc-gI1.

B. Expression of gI in Sf9 Cells

Figure 3A:
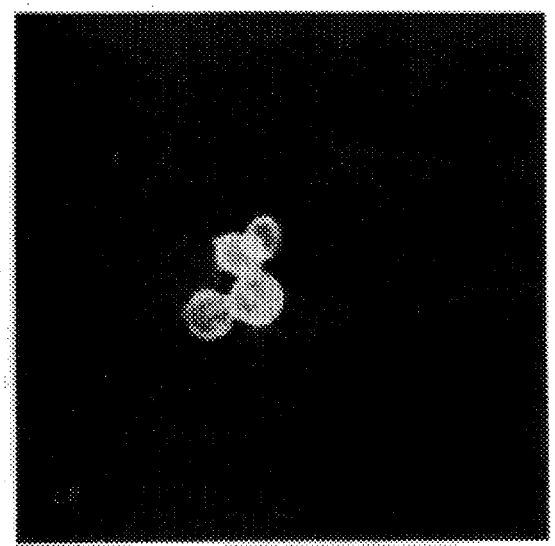
Figure 3B:
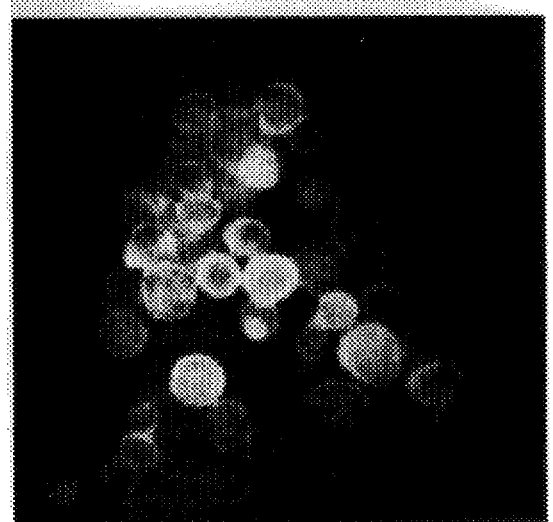
Figure 3C:
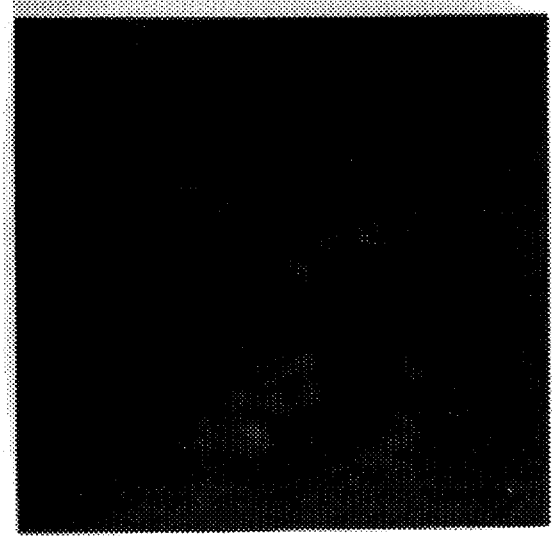

To analyze the size of the baculovirus expressed gI, confluent monolayers of Sf9 cells were infected at a multiplicity of 10 PFU/cell with the baculovirus recombinant vAc-gI1. Total protein extracts were run on 10% SDS-PAGE and analyzed by Western blotting using Fd69 monoclonal antibody against gI. Two bands of 52 and 56 kDa reacted strongly with the gI specific antibody (FIG. 3, lanes 2 and 3). In addition, these bands were more prominent at 72 hr post infection (lane 3) then at 48 hr post infection (lane 2). None of these bands was seen in wild type baculovirus infected cells (lane 1) or mock-infected Sf9 cells.

C. Glycosylation of gI

To demonstrate that the expressed gI underwent glycosylation, tunicamycin treatment was done to prevent N-glycosylation in infected Sf9 cells. Infected cells were treated with 4 µg tunicamycin/ml of media from 0–48 hr post infection, and total cell extracts were analyzed by Western blots using anti-gI monoclonal antibody. The tunicamycin treatment (FIG. 3, lane 4) increased the mobility of gI relative to the control (lanes 2 and 3), indicating that the 52 and 56 kDa polypeptides both contain N-linked sugars. This result indicates that like native gI, the untreated recombinant gI was glycosylated.

Following Endo-H treatment, the 52 and 56 kDa bands were replaced by a polypeptide with an apparent molecular weight of 50 kDa (FIG. 3, lane 5). These results indicate that the recombinant gI was N-glycosylated and contained high mannose sugars.

D. Localization of Recombinant gI in Insect Cells

To determine whether the expressed gI was transported to the cell surface, vAc-gI1 infected Sf9 cells were examined by indirect immunofluorescence antibody staining using monoclonal antibody to gI (FIG. 3). Total cell immunofluorescence was readily observed in recombinant-infected cells (Panel A). To look specifically for gI on the cell surface, indirect immunofluorescence antibody staining was done on cells prior to fixation (Panel B). The surface fluorescence on vAc-gI1 infected cells was strong and comparable to that observed for permeabilized fixed cells. Only background level immunofluorescence was seen in cells infected with the wild-type baculovirus, AcNPV, (Panel C) or mock-infected Sf9 cells. This indicates that the expressed gI was transported to the cell surface.

E. Neutralizing Antibody Response

Balb/C mice were immunized three times subcutaneously and intraperitoneally with whole insect cells expressing gI. Three weeks after the final vaccination, mice were bled. Pooled sera from 20 mice inoculated with the recombinant gI was heat-inactivated and reacted with HSV-1 in the presence of either fresh or heat-inactivated complement. Antibody from the recombinant gI vaccinated mice neutralized HSV-1 infectivity; however, in the presence of fresh complement, the level of neutralization was higher than in the presence of heat-inactivated complement. No neutralizing antibody was produced in mock (AcNPV) vaccinated animals.

F. Vital challenge

Vaccinated mice were challenged by intraperitoneal injection with HSV-1 strain McKrae ($2 \times 10^6$ PFU) three weeks after the final inoculation. As illustrated in Table I below, 60% of the mock vaccinated mice died within 14 days, while 90% of mice vaccinated with expressed gI survived. In the positive control group, 100% of mice immunized with KOS were protected (Table I). Our results suggest that the inoculation of naive animals with baculovirus expressed gI protected mice from lethal intraperitoneal challenge with HSV-1.

TABLE I

Immunization of mice with a recombinant baculovirus expressing HSV-I gI

| Immunization | No. of survivors total no.[a] | % Survival | Neutralization titer[b] + Complement | − Complement |
|---|---|---|---|---|
| Baculovirus GI | 18/20 | 90 | 167 | 91 |
| KOS | 11/11 | 100 | >320 | >320 |
| Mock | 7/18 | 39 | <10 | <10 |

[a]Survival rates (protection) of the baculovirus gI recombinant- and KOS-vaccinated mice were significantly different from the mock vaccination survival rate (Fisher's exact test; P = 0.01).
[b]Neutralization titers are expressed as the reciprocal geometric means of the dilution that produce a 50% reduction in plaque numbers.

In summary, the present invention involves the high level expression of gI in a baculovirus expression system. The gI in this system was glycosylated and transported to the cell surface. Vaccination of naive mice with recombinant gI resulted in the production of complement-dependent and complement-independent neutralizing antibodies to HSV-1. In addition, mice vaccinated with gI were protected from lethal HSV-1 challenge, making gI a useful and Important component in any subunit vaccine against HSV-1.

G. Purification Of gI

The baculovirus expressed gI of the present invention may be purified for human use according to standard techniques, including but not limited to, immunoaffinity chromatography and collection of secreted truncated gI from the supernatant medium of cell cultures. The gI purified by these procedures should be free from contamination by other products or proteins.

1. Immunoaffinity chromatography

The gI protein can be purified in roller bottles by sequential steps of lentil lectin chromatography, immunoaffinity chromatography and concentration by ultrafiltration. For the first step, 2 liters of conditioned medium can be supplemented with 1 mM PMSF and 0.5% aprotinin and then loaded onto a 30-ml column of lentil lectin-Sepharose-4B (Sigma Chemical Co., St. Louis, Mo.) at a flow-rate of 50 ml/h. The column can be washed sequentially with 100 ml of PBS and 100 ml of PBS containing 0.5M NaCl. The bound fraction can be eluted with PBS containing 0.5M NaCl, 0.5M α-methylmannoside, 0.1% Triton X-100, and 0.5% aprotinin, and fractions can be assayed for gI by enzyme-linked immunosorbent assay (ELISA).

The peak column fractions can be pooled and applied to a 10-ml immunoaffinity column prepared by linking 70 mg of a rabbit anti-gI polyclonal antibody to cyanogen bromide-activated Sepharose 4B. The gI-specific rabbit anti serum was raised against gI protein, which was purified by preparative SDS-polyacrylamide gel electrophoresis from HSV-1 infected Vero cell lysates. Prior to coupling, an IgG-enriched fraction can be prepared from the gI-specific rabbit anti serum by precipitation with 33% saturated ammonium sulfate. Following application of the lectin column eluate to the immunoaffinity column, the column can be washed consecutively with 20 ml of 10 mM Tris hydrochloride, pH 7.5, and 10 ml of LB without SDS and BSA and then with 30 ml of 10 mM Tris hydrochloride, pH 7.5–0.5M NaCl. The bound fraction can be eluted with 3M ammonium thiocyanate, pH 7.5, and the gI protein peak can be detected by ELISA and Western analysis. The peak fractions can be concentrated and equilibrated in storage buffer (100 mM NaCl, mM Tris hydrochloride, pH 7.5, 1 mM EDTA, 7.5% glycerol) by ultrafiltration with a PM10 membrane (Amicon Corp., Danvers, Mass.). To remove protein absorbed to the membrane surface, the membrane can be washed with storage buffer plus 0.1% Triton X-100, and this wash can then be combined with the initial concentrated fraction.

2. Collection of the secreted truncated gI

The procedures for the collection of a secreted form of gI are known in the art and will therefore not be repeated here. Essentially, however, the fragment encoding the transmembrane anchor sequence can be excised from the gI gene. The deleted gI gene can then be reconstructed by self-ligation to put in frame sequence coding for the extra membrane and C-terminal intracytoplasmic domains. The product can be detected after transfection by immuno-precipitation of the supernatant medium of cell cultures with anti-gI monoclonal antibody.

H. Pharmaceutical Compositions

The gI of the present invention can be formulated according to known methods to prepare pharmaceutically useful compositions in admixture with a pharmaceutically acceptable carrier vehicle. Suitable vehicles and their formulation are described for example in *Remington's Pharmaceutical Sciences* by E. W. Martin. These compositions will contain an effective amount of gI together with a suitable amount of vehicle in order to prepare pharmaceutically acceptable compositions suitable for effective administration to the host.

For purely descriptive and not limiting purposes, several examples of a pharmaceutical preparation of gI for parenteral administration prepared according to the present invention is described.

The vaccine may be supplied as a single dose vial of lyophilized baculovirus expressed HSV-1 gI, alone or in combination with one or more HSV-1 glycoproteins, and a vial of diluent with alum. Alternatively, the vaccine may be supplied in a multidose vial, and a vial of diluent with alum.

The invention being described, it is clear that these methods can be modified, which modifications do not diverge from the spirit and purpose of the invention and which would be apparent to one skilled in the art. It is therefore understood that the present invention is not to be construed as limited to such, but rather to the lawful scope of the appended claims.

We claim:

1. A vaccine against Herpes Simplex Virus infection, comprising Herpes Simplex Virus Type 1 (HSV-1) gI produced by the expression of a recombinant baculovirus having a genetic construct which comprises:

a) a gene sequence encoding at least one of a full length HSV-1 gI (SEQ ID No. 1) and HSV-1 gI truncated by removal of a fragment encoding the transmembrane anchor sequence; and b) a promoter sequence wherein said gI gene sequence is functionally linked to the regulatory elements of said promoter, and wherein said promoter is operative in a baculovirus expression system.

2. The vaccine of claim 1, wherein the genetic construct comprises pAc-gI.

3. A vaccine for the treatment or prevention of Herpes Simplex Virus 1 infection comprising at least one of full length Herpes Simplex Virus Type 1 (HSV-1) gI and HSV-1 gI truncated by removal of the transmembrane anchor sequence.

4. The vaccine of claim 1, further comprising a pharmaceutically acceptable carrier.

5. The vaccine of claim 1, further comprising at least one adjuvant.

6. The vaccine of claim 5, wherein the adjuvant is selected from the group consisting of alum, Freund's, muramyl tripeptide phosphatidyl ethanolamine, and immunostimulating complexes.

7. The vaccine of claim 3, further comprising a pharmaceutically acceptable carrier.

8. The vaccine of claim 3, further comprising at least one adjuvant.

9. The vaccine of claim 8 wherein the adjuvant is selected from the group consisting of alum, Freund's, muramyl tripeptide phosphatidyl ethanolamine, and immunostimulating complexes.

10. The vaccine of claim 1, wherein the promoter is a polyhedron gene promoter.

11. A process for preparing a vaccine against Herpes Simplex Virus 1 infection, comprising the steps of:

preparing a recombinant baculovirus having a genetic construct which comprises a gene sequence encoding at least one of a full length Herpes Simplex Virus Type 1 (HSV-1) gI (SEQ ID No. 1) and HSV-1 gI truncated by removal of a fragment encoding the transmembrane anchor sequence, and a promoter sequence wherein said gI gene sequence is functionally linked to the regulatory elements of said promoter, and wherein said promoter is operative in a baculovirus expression system;

introducing the recombinant baculovirus into a first set of host cells;

culturing the host cell; and recovering said HSV-1 gI from the culture.

12. The processes of claim 11, further comprising the step of formulating an emulsion comprising HSV-1 gI and a pharmaceutically acceptable carrier.

13. The process of claim 12, wherein the emulsion includes at least one adjuvant.

14. The process of claim 13, wherein the adjuvant is selected from the group consisting of alum, Freund's, muramyl tripeptide phosphatidyl ethanolamine, and immunostimulating complexes.

15. The process of claim 11, wherein the recombinant baculovirus is prepared by integrating the genetic construct into the baculovirus genome.

16. The process of claim 15, wherein the genetic construct comprises pAc-gI.

17. The process of claim 11, wherein said first set of host cells is an insect cell which expresses said genetic construct.

18. The process of claim 17, wherein the insect cell is derived from *Spodoptera frugiperda*.

19. The process of claim 11 wherein said HSV-1 gI is obtained without contamination by other products or proteins.

20. The process of claim 11, wherein the promoter is a polyhedron gene promoter.

21. The process of claim 11, further comprising the steps of:

cotransfecting a second set of host cells with the genetic construct and a wild type baculovirus DNA; and screening the second set of host cells to identify cells harboring recombinant baculovirus.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1190 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TATAAATACG  GATCCCGGGA  TGCCGTGCCG  CCCGTTGCAG  GGCCTGGTGC  TCGTGGGCCT    60
CTGGGTCTGT  GCCACCAGCC  TGGTTGTCCG  TGGCCCCACG  GTCAGTCTGG  TATCAAACTC   120
ATTTGTGGAC  GCCGGGGCCT  TGGGGCCCGA  CGGCGTAGTG  GAGGAAGACC  TGCTTATTCT   180
CGGGGAGCTT  CGCTTTGTGG  GGGACCAGGT  CCCCCACACC  ACCTACTACG  ATGGGGCGT    240
AGAGCTGTGG  CACTACCCCA  TGGGACACAA  ATGCCCACGG  GTCGTGCATG  TCGTCACGGT   300
GACCGCGTGC  CCACGTCGCC  CCGCCGTGGC  ATTCGCCCTG  TGTCGCGCGA  CCGACAGCAC   360
TCACAGCCCC  GCATATCCCA  CCCTGGAGCT  CAATCTGGCC  CAACAGCCGC  TTTTGCGGGT   420
CCAGAGGGCA  ACGCGGGACT  ATGCCGGGGT  GTACGTGTTA  CGCGTATGGG  TCGGTGACGC   480
GCCAAACGCC  AGCCTGTTTG  TCCTGGGGAT  GGCCATAGCC  GCCGAAGGGA  CTCTGGCGTA   540
CAACGGCTCG  GCCTATGGCT  CCTGCGACCC  GAAACTGCTT  CCGTCTTCGG  CCCCGCGTCT   600
GGCCCCGGCG  AGCGTATACC  AACCCGCCCC  TAACCAGGCC  TCCACCCCCT  CGACCACCAC   660
CTCCACCCCC  TCGACCACCA  TCCCCGCTCC  CTCGACCACC  ATCCCCGCTC  CCCAAGCATC   720
GACCACGCCC  TTCCCCACGG  GAGATCCAAA  ACCACAACCT  CCCGGGGTCA  ACCACGAACC   780
CCCATCTAAT  GCCACGCGAG  CGACCCGCGA  CTCGCGATAC  GCGCTAACGG  TGACCCAGAT   840
AATCCAGATA  GCCATCCCCG  CGTCCATCAT  AGCCCTGGTG  TTTCTGGGGA  GCTGTATTTG   900
CTTTATACAC  AGATGTCAAC  GCCGCTACCG  ACGCTCCCGT  CGCCCGATTT  ACAGCCCCA    960
GATGCCCACG  GGCATCTCAT  GCGCGGTGAA  CGAAGCGGCC  ATGGCCCGCC  TCGGAGCCGA  1020
GCTCAAATCG  CATCCGAGCA  CCCCCCCCAA  ATCCCGGCGC  CGGTCGTCAC  GCACGCCAAT  1080
GCCCTCCCTG  ACGGCCATCG  CCGAAGAGTC  GGAGCCCGCT  GGGGCGGCTG  GGCTTCCGAC  1140
GCCCCCCGTG  GACCCCACGA  CACCCACCCC  AACGCCTCCC  CTGTTGGTAT              1190
```